US005786454A

United States Patent [19]

Waksman et al.

[11] Patent Number: 5,786,454
[45] Date of Patent: Jul. 28, 1998

[54] MODIFIED SH2 DOMAINS

[75] Inventors: Gabriel Waksman, University City; Andrey Shaw, St. Louis, both of Mo.

[73] Assignee: Washington University School of Medicine, St. Louis, Mo.

[21] Appl. No.: 308,086

[22] Filed: Sep. 16, 1994

[51] Int. Cl.[6] ............................ C07K 14/00; C07K 14/82
[52] U.S. Cl. ............................................ 530/402; 530/350
[58] Field of Search ................................ 530/350, 402; 435/69.1

[56] References Cited

U.S. PATENT DOCUMENTS 5,352,660  10/1994  Pawson .

OTHER PUBLICATIONS

Mayer et al., *Mol. Cell. Bio*, vol. 12, pp. 609–618, 1992.
Marengere et al., *JBC*, vol. 267, pp. 22779–22786, 1992.
Birge and Hanafusa, "Closing in on SH2 Specificity," *Science* 262:1522 (1993).
Cantley et al., "Oncogenes and Signal Transduction," *Cell* 64:281–302 (1991).
Chan, A.C., et al., "ZAP-70: A 70 kd Protein–Tyrosine Kinase That Associates with the TCR Chain," *Cell* 71:649–662 (1992).
Darnell, J.J., et al., "Jak–STAT Pathways and Transcriptional Activation in Response to IFNs and Other Extracellular Signaling Proteins," *Science* 264:1415–1421 (1994).
Feng, G.S. and Pawson, T., "Phosphotyrosine phosphatases with SH2 domains: regulators of signal transduction," *Trends in Genetics* 10:54–58 (1994).
Graham and VanDer, "A New Technique for the Assay of Infectivity of Human Adenovirus 5 DNA," *Virology* 52:456 (1973).
Kimura and Dulbecco, "Isolation and Characterization of Temperature–Sensitive Mutants of Simian Virus 40," *Virology* 49:394 (1972).
Lowenstein, E.J. et al., "The SH2 and SH3 Domain–Containing Protein GRB2 Links Receptor Tyrosine Kinases to ras Signaling," *Cell* 70:431–442 (1992).
Matsuda,et al., "Binding of Transforming Protein, P47$^{gag-crk}$, to a Broad Range of Phosphotyrosine–Containing Proteins," *Science* 248:1537–1539 (1990).
Matthews, R.J., et al., "Characterization of Hematopoietic Intracellular Protein Tyrosine Phosphatases: Description of a Phosphatase Containing an SH2 Domain and Another Enriched in Proline–, Glutamic Acid–, Serine–, and Threonine–Rich Sequences," *Mol. Cell Biol.* 12:2396–2405 (1992).
Mayer, et al., "A novel viral oncogene with structural similarity to phospholipase C," *Nature* 332:272–275 (1988).
Mayer and Hanabusa, "Mutagenic Analysis of the v–crk Oncogene: Requirement for SH2 and SH3 Domains and Correlation between Increased Cellular Phosphotyrosine and Transformation," *J. Virol.* 64:3581–3589 (1990).
Miller, A.D., et al., "Use of Retroviral Vectors for Gene Transfer and Expression," *Methods in Enzymology* 217:581(1993).

Pan, M.G., et al., "G Protein Activation of a Hormone–Stimulated Phosphatase in Human Tumor Cells," *Science* 256:1215–1217 (1992).
Panayotou, G., et al., "Interactions between Sh2 Domains and Tyrosine–Phosphorylated Platelet–Derived Growth Factor β–Receptor Sequences: Analysis of Kinetic Parameters by a Novvel Biosensor–Based Approach," *Mol. Cell. Biol.* 13:3567–3576 (1993).
Pawson and Schlesinger, "SH2 and SH3 domains," *Current Biology* 3:434–442 (1993).
Pelicci, G., "A Novel Transforming Protein (SHC) with an SH2 Domain is Implicated in Mitogenic Signal Transduction," *Cell* 70:93–104 (1992).
Potter, "Enhancer–dependent expression of human κ immunoglobulin genes introduced into mouse pre–B lymphocytes by electroporation," *Proc. Natl. Acad. Sci. USA* 81:7161 (1984).
Sandri–Goldin, et al., "High–Frequency Transfer of Cloned Herpes Simplex Virus Type 1 Sequences to Mammalian Cells by Protoplast Fusion," *Molec. Cell Biol.* 1:743 (1981).
Skolnik, E.Y., "Cloning of PI3 Kinase–Associated p85 Utilizing a Novel Method for Expression/Cloning of Target Proteins for Receptor Tyrosine Kinases," *Cell* 65:83–90 (1991).
Sompayrac and Danna, "Efficient infection of monkey cells with DNA of simian virus 40," *Proc. Natl. Acad. Sci. USA* 78:7575 (1981).
Songyang et al., "SH2 Domains Recognize Specific Phosphopeptide Sequences," *Cell* 72:767–778 (1993).
Taniguchi, T. et al., "Molecular Cloning of a Porcine Gene syk That Encodes a 72–kDa Protein–Tyrosine Kinase Showing High Susceptibility to Proteolysis," *J. Biol. Chem.* 266:15790–15796 (1991).
Vogel, U.S., et al., "Cloning of bovine GAP and its interaction with oncogenic ras p21," *Nature* 335:90–93 (1988).
Waksman et al., "Crystal structure of the phosphotyrosine recognition domain SH2 of v–src complexed with tyrosine-–phosphorylated peptides", *Nature* 358:646–653 (1992).
Waksman et al., "Binding of a High Affinity Phosphotyrosyl Peptide to the Src SH2 Domain: Crystal Structures of the Complexed and Peptide–free Forms," *Cell* 72:779–790 (Mar. 1993).
White, M.F., "The IRS–1 Signalling System", *Current Opinion in Genetics & Development* 4:47–54 (1994).
Zhong, Z. et al., "Stat3 and Stat4: Members of the family of signal transducers and activators of transcription," *Proc. Natl. Acad. Sci. USA* 91:4806–4810 (1994).

*Primary Examiner*—Marianne P. Allen
*Assistant Examiner*—Stephen Gucker
*Attorney, Agent, or Firm*—Arnall Golden & Gregory, LLP

[57] ABSTRACT

Modified SH2 domains of intracellular proteins and methods of use, wherein the SH2 domains are modified to include an altered binding site for a signal transduction protein. The binding site is altered to either change the specificity of the SH2 domain for a signal transduction protein that is not the natural ligand or to include a reactive group, such as a reactive amino acid, that reacts with a phosphorylated amino acid of the signal transduction protein. The modified SH2 domains are useful as research tools or in methods for inactivating or inhibiting signal transduction proteins, especially those that contribute to disease or disorders such as cancer or for targeting specific SH2 domains for diagnostics.

19 Claims, 10 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO:1:

Tyr Glu Glu Ile Ser Pro Lys
                  5

( 2 ) INFORMATION FOR SEQ ID NO:2:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: protein ( x i ) SEQUENCE DESCRIPTION: SEQ ID NO:2:

Tyr Met Asp Met Ser Pro Lys
                  5

( 2 ) INFORMATION FOR SEQ ID NO:3:

( i ) SEQUENCE CHARACTERISTICS:
      ( A ) LENGTH: 98 amino acids
      ( B ) TYPE: amino acid
      ( D ) TOPOLOGY: linear ( i i ) MOLECULE TYPE: protein ( x i ) SEQUENCE DESCRIPTION: SEQ ID NO:3:

Trp Tyr Phe Gly Lys Ile Thr Arg Arg Glu Ser Glu Arg Leu Leu Leu
                  5                    10                      15

Asn Pro Glu Asn Pro Arg Gly Thr Phe Leu Val Arg Glu Ser Glu Thr
             20                     25                  30

Thr Lys Gly Ala Tyr Cys Leu Ser Val Ser Asp Phe Asp Asn Ala Lys
             35                  40              45

Gly Leu Asn Val Lys His Tyr Lys Ile Arg Lys Leu Asp Ser Gly Gly
         50                  55                  60

Phe Tyr Ile Thr Ser Arg Thr Gln Phe Ser Ser Leu Gln Gln Leu Val
65                      70                  75                  80

Ala Tyr Tyr Ser Lys His Ala Asp Gly Leu Cys His Arg Leu Thr Asn
                 85                  90                  95

Val Cys ( 2 ) INFORMATION FOR SEQ ID NO:4:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Trp Phe Phe Lys Asn Leu Ser Arg Lys Asp Ala Glu Arg Gln Leu Leu
                  5                  10                  15
Ala Pro Gly Asn Thr His Gly Ser Phe Leu Ile Arg Glu Ser Glu Ser
             20                  25                  30
Thr Ala Gly Ser Phe Ser Leu Ser Val Arg Asp Phe Asp Gln Asn Gln
         35                  40                  45
Gly Glu Val Val Lys His Tyr Lys Ile Arg Asn Leu Asp Asn Gly Gly
     50                  55                  60
Phe Tyr Ile Ser Pro Arg Ile Thr Phe Pro Gly Leu His Asp Leu Val
65                  70                  75                  80
Arg His Tyr Thr Asn Ala Ser Asp Gly Leu Cys Thr Arg Leu Ser Arg
                 85                  90                  95
Pro Cys
```

( 2 ) INFORMATION FOR SEQ ID NO:5:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Trp Tyr His Gly Pro Val Ser Arg Asn Ala Ala Glu Tyr Leu Leu Ser
                  5                  10                  15
Ser Gly Ile Asn Gly Ser Phe Leu Val Arg Glu Ser Glu Ser Ser Pro
             20                  25                  30
Gly Gln Arg Ser Ile Ser Leu Arg Tyr Glu Gly Arg Val Tyr His Tyr
         35                  40                  45
Arg Ile Asn Thr Ala Ser Asp Gly Lys Leu Tyr Val Ser Ser Glu Ser
     50                  55                  60
Arg Phe Asn Thr Leu Ala Glu Leu Val His His His Ser Thr Val Ala
65                  70                  75                  80
Asp Gly Leu Ile Thr Thr Leu His Tyr Pro Ala
                 85                  90
```

( 2 ) INFORMATION FOR SEQ ID NO:6:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Trp Tyr His Lys Leu Asp Arg Thr Ile Ala Glu Glu Arg Leu Arg Gln
                  5                  10                  15
Ala Gly Lys Ser Gly Ser Tyr Leu Ile Arg Glu Ser Asp Arg Arg Pro
             20                  25                  30
```

```
Gly  Ser  Phe  Val  Leu  Ser  Phe  Leu  Ser  Gln  Thr  Asn  Val  Val  Asn  His
          35                       40                      45

Phe  Arg  Ile  Ile  Ala  Met  Cys  Gly  Asp  Tyr  Tyr  Ile  Gly  Gly  Arg  Arg
     50                      55                      60

Phe  Ser  Ser  Leu  Ser  Asp  Leu  Ile  Gly  Tyr  Tyr  Ser  His  Val  Ser  Cys
65                       70                      75                           80

Leu  Leu  Lys  Gly  Glu  Lys  Leu  Leu  Tyr  Pro
               85                       90
```

( 2 ) INFORMATION FOR SEQ ID NO:7:

( i ) SEQUENCE CHARACTERISTICS:
        ( A ) LENGTH: 90 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Trp  Phe  His  Gly  Lys  Ile  Ser  Lys  Gln  Glu  Ala  Tyr  Asn  Leu  Leu  Met
               5                        10                          15

Thr  Val  Gly  Gln  Ala  Cys  Ser  Phe  Leu  Val  Arg  Pro  Ser  Asp  Asn  Thr
               20                       25                      30

Pro  Gly  Asp  Tyr  Ser  Leu  Tyr  Phe  Arg  Thr  Ser  Glu  Asn  Ile  Gln  Arg
          35                       40                      45

Phe  Lys  Ile  Cys  Pro  Thr  Pro  Asn  Asn  Gln  Phe  Met  Met  Gly  Gly  Arg
     50                      55                      60

Tyr  Tyr  Asn  Ser  Ile  Gly  Asp  Ile  Ile  Asp  His  Tyr  Arg  Lys  Glu  Gln
65                       70                      75                           80

Ile  Val  Glu  Gly  Tyr  Tyr  Leu  Lys  Glu  Pro
               85                       90
```

( 2 ) INFORMATION FOR SEQ ID NO:8:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Trp  Tyr  Trp  Gly  Asp  Ile  Ser  Arg  Glu  Glu  Val  Asn  Glu  Lys  Leu  Arg
               5                        10                          15

Asp  Thr  Ala  Asp  Gly  Thr  Phe  Leu  Val  Arg  Asp  Ala  Ser  Thr  Lys  Met
               20                       25                      30

His  Gly  Asp  Tyr  Thr  Leu  Thr  Leu  Arg  Lys  Gly  Gly  Asn  Asn  Lys  Leu
          35                       40                      45

Ile  Lys  Ile  Phe  His  Arg  Asp  Gly  Lys  Tyr  Gly  Phe  Ser  Asp  Pro  Leu
     50                      55                      60

Thr  Phe  Asn  Ser  Val  Val  Glu  Leu  Ile  Asn  His  Tyr  Arg  Asn  Glu  Ser
65                       70                      75                           80

Leu  Ala  Gln  Tyr  Asn  Pro  Lys  Leu  Asp  Val  Lys  Leu  Leu  Tyr  Pro
               85                       90                          95
```

( 2 ) INFORMATION FOR SEQ ID NO:9:

( i ) SEQUENCE CHARACTERISTICS:
        ( A ) LENGTH: 94 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Trp Asn Val Gly Ser Ser Asn Arg Asn Lys Ala Glu Asn Leu Leu Arg
                  5                  10                      15
Gly Lys Arg Asp Gly Thr Phe Leu Val Arg Glu Ser Ser Lys Gln Gly
            20                  25                  30
Cys Tyr Ala Cys Ser Val Val Val Asp Gly Glu Val Lys His Cys Val
            35              40                  45
Ile Asn Lys Thr Ala Thr Gly Tyr Gly Phe Ala Glu Pro Tyr Asn Leu
    50                  55                      60
Tyr Ser Ser Leu Lys Glu Leu Val Leu His Tyr Gln His Thr Ser Leu
65                  70                  75                      80
Val Gln His Asn Asp Ser Leu Asn Val Thr Leu Ala Tyr Pro
                85                  90
```

( 2 ) INFORMATION FOR SEQ ID NO:10:

( i ) SEQUENCE CHARACTERISTICS:
( A ) LENGTH: 107 amino acids
( B ) TYPE: amino acid
( D ) TOPOLOGY: linear ( i i ) MOLECULE TYPE: protein ( x i ) SEQUENCE DESCRIPTION: SEQ ID NO:10:

```
Trp Phe His Gly Lys Leu Gly Ala Gly Arg Asp Gly Arg His Ile Ala
                  5                  10                      15
Glu Arg Leu Leu Thr Glu Tyr Cys Ile Glu Thr Gly Ala Pro Asp Gly
            20                  25                  30
Ser Phe Leu Val Arg Glu Ser Glu Thr Phe Val Gly Asp Tyr Thr Leu
            35              40                  45
Ser Phe Trp Arg Asn Gly Lys Val Gln His Cys Arg Ile His Ser Arg
    50                  55                  60
Gln Asp Ala Gly Thr Pro Lys Phe Phe Leu Thr Asp Asn Leu Val Phe
65                  70                  75                      80
Asp Ser Leu Tyr Asp Leu Ile Thr His Tyr Gln Gln Val Pro Leu Arg
                85                  90                  95
Cys Asn Glu Phe Glu Met Arg Leu Ser Glu Pro
                100                 105
```

( 2 ) INFORMATION FOR SEQ ID NO:11:

( i ) SEQUENCE CHARACTERISTICS:
( A ) LENGTH: 88 amino acids
( B ) TYPE: amino acid
( D ) TOPOLOGY: linear ( i i ) MOLECULE TYPE: protein ( x i ) SEQUENCE DESCRIPTION: SEQ ID NO:11:

```
Trp Tyr His Ala Ser Leu Thr Arg Ala Gln Ala Glu His Met Leu Met
                  5                  10                      15
Arg Val Pro Arg Asp Gly Ala Phe Leu Val Arg Lys Arg Asn Glu Pro
            20                  25                  30
Asn Ser Tyr Ala Ile Ser Phe Arg Ala Glu Gly Lys Ile Lys His Cys
            35              40                  45
Arg Val Gln Gln Glu Gly Gln Thr Val Met Leu Gly Asn Ser Glu Phe
    50                  55                  60
```

```
Asp  Ser  Leu  Val  Asp  Leu  Ile  Ser  Tyr  Tyr  Glu  Lys  His  Pro  Leu  Tyr
65                        70                      75                        80

Arg  Lys  Met  Lys  Leu  Arg  Tyr  Pro
                    85
```

MODIFIED SH2 DOMAINS

This relates to the field of cell biology and more particularly relates to protein biochemistry and signal transduction.

BACKGROUND OF THE INVENTION

Signal transduction is the internalization and propagation of a signal, commonly caused by the binding of a ligand with a receptor on the surface of or within a cell. Signal transduction works through phosphorylation and dephosphorylation of tyrosine, serine, or threonine residues on proteins. One cause of cancer is a defect in one or more proteins, or oncoproteins, involved in signal transduction.

Protein-tyrosine kinases are enzymes that provide a central switching mechanism in cellular signal transduction pathways by catalyzing the phosphorylation of tyrosine residues in specific proteins. Although the first tyrosine kinase was discovered as the protein product of the Rous sarcoma virus oncogene, $p60^{v-src}$, the normal cellular forms of these enzymes occur either as transmembrane growth hormone receptors or as cytosolic non-receptor proteins.

Normally a ligand, such as a growth hormone or cytokine, binds to the extracellular domain of a transmembrane protein, such as a receptor protein-tyrosine kinase, inducing dimerization of the receptor, which leads to activation of the intrinsic tyrosine kinase and intermolecular autophosphorylation of tyrosine residues in the cytoplasmic region of the protein. This autophosphorylation causes a cascade of events leading to the appropriate response.

Transmission of the ligand-induced signal to other components of the cell depends on the recognition of the phosphorylated tyrosines on the receptor protein-tyrosine kinase by certain cytoplasmic signal transduction proteins. These proteins have distinctive domains containing approximately 100 amino-acid residues, which are known as SH2 (src homology-2) domains. SH2 domains have evolved to recognize phosphorylated tyrosines with specificity. They complement the action of the catalytic kinase activity by communicating the phosphorylation states of signal transduction proteins to elements of the signalling pathway. SH2 domains and their role in determining the specificity of protein-protein interactions are reviewed by Pawson and Schlesinger, *Current Biology* 3:434–442 (1993)

SH2 domains are found in cytoplasmic non-receptor tyrosine kinases as well as in a number of other proteins that play key roles in signal transduction. Signal transduction proteins that are not tyrosine kinases but which contain SH2 domains include, for example, phospholipase C-γ1, the p85 subunit of phosphatidylinositol-3-OH kinase, ras GTPase-activating protein (GAP), and protein-tyrosine phosphatases. In each of these proteins, the sequence of the SH2 domain is highly conserved and is thought to be involved in either localizing the protein to tyrosine-phosphorylated proteins or controlling its activity.

The functional importance of the SH2 domain in the signal transduction pathway was determined in studies on the oncogene product $p47^{gag-crk}$, which causes cellular transformation and increased levels of tyrosine phosphorylation. $p47^{gag-crk}$ does not contain a kinase domain, but contains SH2 and SH3 domains. The SH2 domain is solely responsible for association with tyrosine phosphorylated proteins and is required for cellular transformation as discussed by Mayer et al. *Nature* 332:272–275 (1988), Matsuda et al., *Science* 248:1537–1539 (1990), and Mayer et al., *J. Virol.* 64:3581–3589 (1990). The crystal structure of the src SH2 domain in a complex with several phosphotyrosine-containing peptides has been determined as described by Waksman et al., "Crystal structure of the phosphotyrosine recognition domain SH2 of v-src complexed with tyrosine-phosphorylated peptides", *Nature* 358:646–653 (1992).

SH2 domains contain the structural information that allows recognition of the sequence context in which the phosphorylated tyrosine lies, thereby promoting binding specificity and maintaining the required separation of transduction pathways. Cantley and coworkers have demonstrated that residues at the +1, +2 and +3 positions relative to the phosphotyrosine are specifically recognized by SH2 domains. (Cantley et al., *Cell* 64:281–302 (1991). Songyang et al., *Cell* 72:767–778 (1993), which are incorporated by reference herein.)

While normal activation of tyrosine kinases induces cells to proliferate, migrate, or differentiate, aberrant tyrosine kinase activity results in constitutive activation causing the excessive cell growth or proliferation commonly associated with cancer and can also be responsible for pathological conditions such as autoimmune diseases, allergy, and transplant rejection.

It is therefore, an object of the present invention to provide a method for suppressing tyrosine kinase activity.

It is a further object of the present invention to provide modified SH2 domains that target specific signal transduction proteins and therefore target, suppress and inactivate tyrosine kinases.

It is a further object of the present invention to provide SH2-based diagnostic tools to detect phosphorylation events responsible for tyrosine protein kinase activation and therefore cancer.

It is a further object of the present invention to provide modified SH2 domains for screening small organic or inorganic inhibitors capable of competing with pathologically phosphorylated targets and therefore capable of preventing cell proliferation.

It is a further object of the present invention to provide a method for treating pathological conditions caused by signal transduction proteins and constitutive tyrosine kinase activation.

SUMMARY OF THE INVENTION

Modified and highly specific SH2 domains of intracellular proteins and methods of use are provided. SH2 domains are modified to include an altered binding site for a signal transduction protein. The binding site is altered to either change the specificity of the SH2 domain for a signal transduction protein that is not the natural ligand or to include a reactive group that reacts with a phosphorylated amino acid of the signal transduction protein. Most preferably, the SH2 domain is modified in the BG loop, the EF loop, strand βE, strand βD, or strand βD'.

Modified SH2 domains are useful as research tools to study signal transduction in general and for a variety of applications including diagnostics, therapeutics, and drug design. For diagnostic use, modified SH2 domains are engineered to detect aberrant phosphorylation events including those associated with tumor progression of breast and ovarian carcinomas for tumor diagnosis and staging. For therapeutics, SH2 domains are engineered to interfere with signal transduction pathways to treat pathological disorders resulting from aberrant signal transduction pathways such as cancer, autoimmune diseases and allergies. Interference with the signal generated by the signal transducing protein prevents further transmission of the signal to other components of the cell. Preferably, the SH2 domain is modified to bind to an aberrant signal transduction protein, thereby blocking the binding of the wild type SH2 domains, or to inactivate the phosphorylated signal transduction protein by removing a phosphate group. Most preferably, the SH2 domain is modified by replacing a non-reactive amino acid in the binding site with a reactive amino acid. For drug design, modified SH2 domains are used to screen for small molecules that bind with high affinity to those SH2 domains. Such small compounds may then be useful for blocking specific signal transduction pathways by competing against endogenous SH2-containing proteins that would otherwise bind to the phosphorylation site. In cancer or other pathologic conditions where phosphorylation sites are constitutively phosphorylated, such small compounds would "turn off" the signal, thereby acting as therapeutic agents.

BRIEF DESCRIPTION OF THE DRAWINGS

In FIG. 3a, a tyrosine-phosphorylated signal transduction protein sequence is inserted into the peptide binding specificity pocket and the phosphotyrosine binding pocket of an SH2 domain. The X represents any of the 20 possible amino acid residues, Y is a tyrosine residue, N is the N-terminus of a signal transduction protein, C is the C-terminus of a signal transduction protein, and an encircled P indicates phosphorylation of the residue to which it is attached. FIG. 3b is a schematic representation showing the three-dimensional orientation of the interaction of the SH2 domain with the signal transduction protein of FIG. 3a.

In FIG. 5a, an SH2 domain library containing random mutations around the peptide binding specificity pocket is screened for high affinity peptide binding by binding to a sequence XXXpYXXXX, wherein X is any of the 20 possible amino acid residues, Y is a tyrosine residue, p indicates that the tyrosine residue is phosphorylated, and the asterisks represent mutations. FIG. 5b is a schematic representation showing how predetermined mutations engineered in the peptide binding pocket of an SH2 domain produce the required binding specificity. The asterisks represent mutations.

FIG. 9a is a graph showing the relative response of the binding of mutated and wild-type SH2 domains from src and the p85 subunit of PI3-kinase to phosphorylated YEEI peptide as measured by surface plasmon resonance over time in minutes. The peptide pYEEISPK (SEQ ID NO:1) biotinylated on the C-terminal lysine residue was coupled onto a streptavidin coated sensor chip at a concentration of 20 pg/ml. GST fusions of mutated and wild-type SH2 domains were injected at a flow rate of 5 μl/minute. Protein concentrations for mutated src SH2 domains as well as the p85 SH2 domain were adjusted to get equivalent binding signal. "wt" is an abbreviation for wild type src SH2 domains from src, "13" is an abbreviation for the mutant designated M1M3, "12" is an abbreviation for the mutant designated M1M2, "23" is an abbreviation for the mutant designated M2M3, and "P85" is an abbreviation for wild-type p85 SH2 domains. Isotherms obtained for M1M3 are depicted with a dotted line. FIG. 9b is a graph showing the relative response of the binding of mutated and wild-type SH2 domains from src and the p85 subunit of PI3-kinase to phosphorylated YMDM peptide as measured by surface plasmon resonance over time in minutes. The peptide pYMDMSPK (SEQ ID NO:2) biotinylated on the C-terminal lysine residue was coupled onto a streptavidin-coated sensor chip at a concentration of 20 pg/ml. GST fusions of mutated and wild-type SH2 domains were injected at a flow rate of 5 μl/minute. Protein concentrations used were as determined in FIG. 9a, and the abbreviations are the same as in FIG. 9a. Isotherms obtained for M1M3 are depicted with a dotted line. FIG. 9c is a graph showing the relative response of the binding of mutated and wild-type SH2 domains from src and the p85 subunit of PI3-kinase to phosphorylated YMDM peptide as measured by surface plasmon resonance at equal protein concentration. The peptide pYMDMSPK (SEQ ID NO:2) biotinylated on the C-terminal lysine residue was coupled onto a streptavidin coated sensor chip at a concentration of 20 pg/ml. GST fusions of mutated and wild-type SH2 domains were injected at a flow rate of 5 μl/minute. All proteins were injected at a concentration of 200 nM/ml. The abbreviations are the same as in FIG. 9a. Isotherms obtained for M1M3 are depicted with a dotted line.

DETAILED DESCRIPTION OF THE INVENTION

Modified SH2 domains and methods of use are provided. SH2 domains are regions of distinctive amino acid residues of cytoplasmic proteins that bind to phosphorylated amino acids of signal transduction proteins. The modified SH2 domains have altered binding sites for the signal transduction protein. The binding sites are altered to either redirect the specificity of the SH2 domain to a target signal transduction protein for which the SH2 domain is not naturally specific, or the binding sites are altered to include a reactive group that reacts with the signal transduction protein.

Preferably, the SH2 domain is modified to bind with specificity to an aberrant signal transduction protein to either block interaction of the signal transduction protein with an unmodified SH2 domain or to inactivate the signal transduction protein by removing a phosphate group from a phosphorylated amino acid, such as a phosphotyrosine molecule located in the cytoplasmic region of a receptor tyrosine kinase protein. The modified SH2 domain is therefore useful as a therapeutic agent. The modified SH2 domain is also useful as a research tool for studying signal transduction in general or for in vitro diagnosis and staging of proliferative disorders such as cancer.

The SH2 domain is modified by either altering the amino acid sequence of the binding specificity site to confer a predefined peptide binding specificity or by adding one or more reactive groups to the phosphotyrosine binding pocket of the SH2 domain, particularly in the phosphate binding loop, the region of the SH2 domain that binds to the phosphorylated amino acid of the signal transduction protein.

SH2 Domains

SH2 domains are defined herein as distinctive polypeptide regions of cytoplasmic proteins, approximately 100 amino acids in length, having amino acid sequences similar to c-Src and the ability to recognize and bind the phosphorylated amino acid residues of signal transduction proteins such as phosphorylated tyrosines of protein-tyrosine kinases.

Figure 1:
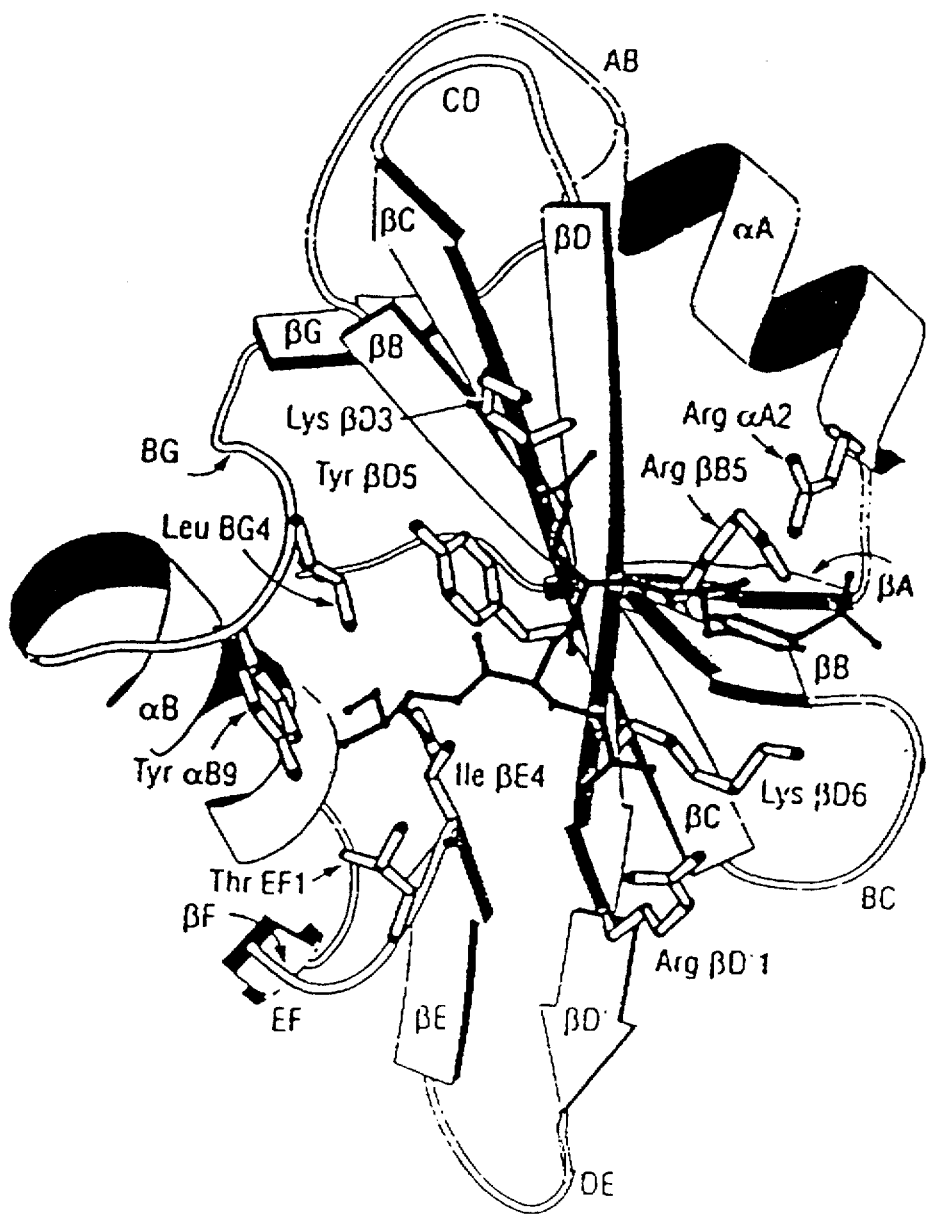
FIG. 1 is a schematic diagram of the src SH2 domain with the elements of secondary structure and important residues labeled. The two α helices are denoted αA and αB, and the β strands are labeled βA through βG. Loops connecting secondary structural elements are denoted by the alphabetical labels of the adjacent helices or strands.
Figure 2:
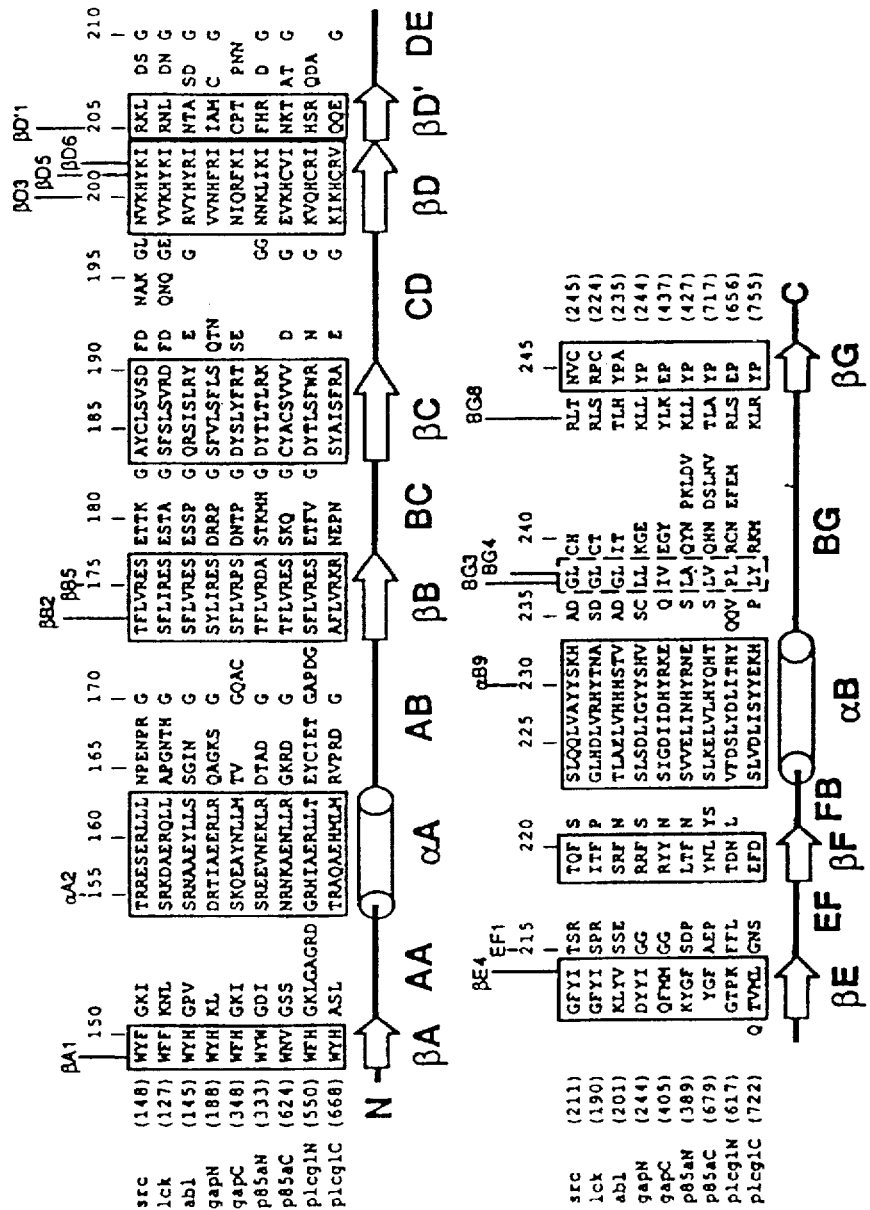
FIG. 2 is an alignment of the amino acids of the SH2 domains src, (SEQ ID NO:3) lck, (SEQ ID NO:4) abl, (SEQ ID NO:5) gapN, (SEQ ID NO:6) gapC, (SEQ ID NO:7) p85aN, (SEQ ID NO:8) p85aC, (SEQ ID NO:9) plcg1N, (SEQ ID NO:10) and plcg1C (SEQ ID NO:11) as depicted by Waksman et al., Cell 72:779–790 (March 1993) (FIG. 2). The secondary structures of the SH2 domains are indicated below the sequences. Peptide residues are numbered relative to the phosphotyrosine.

The crystal structures of the complexed and peptide-free forms of the src SH2 domain have been described by Waksman et al., Cell 72:779–790 (March 1993), which is incorporated by reference herein. A schematic diagram of the src SH2 domain as depicted by Waksman et al. (1993) is shown in FIG. 1 with the elements of secondary structure and important residues labeled according to the following nomenclature. The two α helices are denoted αA and αB, and the β strands are labeled βA through βG. Loops connecting secondary structural elements are denoted by the alphabetical labels of the adjacent helices or strands, such as, for example, AB, BC, etc. Each amino acid residue is denoted by its relative position in a secondary structural element, defined using the alignment described by Waksman et al. (1993), which is shown in FIG. 2. Peptide residues are numbered relative to the phosphotyrosine. The spine of the SH2 domain consists of two distinct β sheets. The two sheets are connected by a single continuous β strand, denoted βD in the first sheet and βD' in the second. The central β sheet (strands B, C, and D) is at the core of the structure and divides the domain into two functionally distinct sides. One side, containing helix αA and one face of the central sheet, is concerned primarily with binding the phosphotyrosine. The other side provides binding sites for the three peptide residues immediately following the phosphotyrosine, and contains helix αB, the smaller β sheet (D', E, and F), a long loop (BG), and the other face of the central sheet. The backbone of the peptide runs along a surface that is perpendicular to the central β sheet. The N- and C-termini of the SH2 domain are located opposite to this peptide-binding surface, with the polypeptide chain entering and leaving the domain at short strands (βA and βG) that hydrogen bond with βB. These two short strands serve to cap the hydrophobic core of the domain. All SH2 domains have the same or highly similar secondary structures.

Figure 3A:
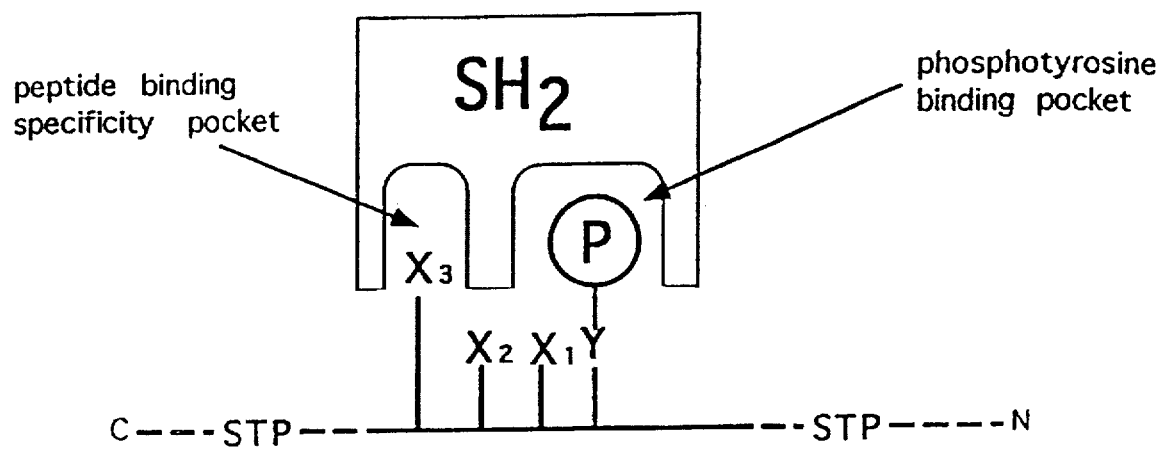
FIG. 3a and FIG. 3b are schematic representations showing how SH2 domains interact with signal transduction proteins in a cell.
Figure 3B:
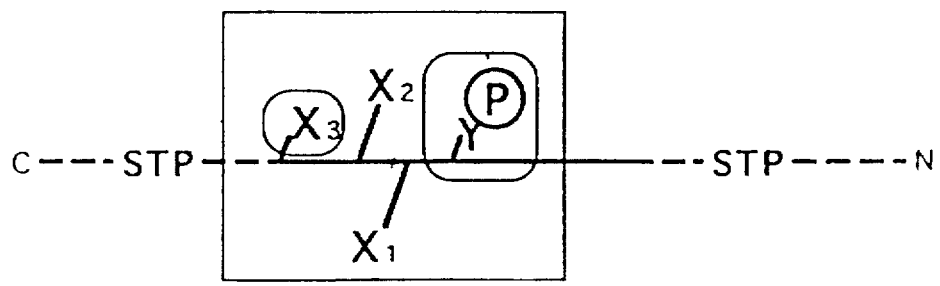

The tyrosine phosphorylated sequences of the signal transduction protein insert into the two binding pockets of SH2 domains: the peptide binding specificity pocket and the phosphotyrosine binding pocket as shown in FIGS. 3a and 3b. When the SH2 domain and signal transduction protein interact, the portions of the SH2 domain three dimensional structure that encompass the BG loop, the EF loop, strand βE, strand βD, and strand βD' make close contacts with the +1, +2 and +3 amino acid positions of the signal transduction protein relative to the phosphotyrosine. These regions are, therefore, optimal sites for alteration.

SH2 domains include regions of cytoplasmic non-receptor tyrosine kinases and other proteins that are highly involved in signal transduction, such as, but not limited to, src (and the src family kinases such as Lck), Abl, phospholipase C-γ1 (reviewed by Cantley et al., Cell 64:281–302 (1991)), the p85 subunit of phosphatidylinositol-3-OH kinase (PIK) (Skolnik, E. Y., Cell 65:83–90 (1991)), ras guanine triphosphatase-activating protein (GAP) (Vogel, U. S. et al., Nature 335:90–93; Lowenstein, E. J. et al., Cell 70:431–442 (1992)), insulin receptor substrate-1 (IRS-1) (White, M. F., "The IRS-1 Signalling System", Current Opinion in Genetics & Development 4:47–54 (1994)), protein-tyrosine phosphatases (Matthews, R. J. et al., Mol. Cell Biol. 12:2396–2405 (1992), Feng, G. S. and Pawson, T., Trends in Genetics 10:54–58 (1994)), grb-2, shc (Pelicci, G., Cell 70:93–104 (1992)), ZAP-70 (Chan, A. C., et al., Cell 71:649–662 (1992), syk (Taniguchi, T. et al., J. Biol. Chem. 266:15790–15796 (1991)), and the transcription factors of the Stat family (Darnell, J. J. et al., Science 264:1415–1421 (1994), Zhong, Z. et al, Proc. Natl. Acad. Sci. USA 91:4806–4810 (1994).

Methods of Modification

SH2 domains may be modified to recognize specific targets by chemical, biochemical and genetic engineering methods. For example, based on crystallographic structure information, specific changes may be engineered into a nucleic acid sequence encoding an SH2 domain using site-directed mutagenesis. This engineered construct is then inserted into a vector and the modified SH2 domains produced by genetic engineering methods known to those skilled in the art. Synthetic reactive amino acid analogues may also be introduced into the phosphotyrosine binding site of the SH2 domain. Alternatively, libraries of sequences containing every possible amino acid in the structural positions responsible for specificity, as described above, may be generated by site-directed mutagenesis. In addition, the number of residues at these positions may be changed by adding or deleting sequences by site-directed mutagenesis. This "library" of sequences containing most or all possible SH2 specificities may then be inserted into a vector and stored and expressed by genetic engineering methods well known to those skilled in the art. The expressed modified SH2 domains may then be screened by methods well known to those skilled in the art for the ability to bind to the appropriate phosphorylated or binding residue of a target signal transduction protein as described in more detail below.

Modifications resulting in altered specificity

The determinants of the SH2 domain responsible for peptide binding specificity can be altered to confer specificity for a signal transduction protein that is not the natural ligand. Alterations are made in the region of the SH2 domain that recognizes or binds to the target signal transduction protein. Preferably, the modifications are made in the region described by those skilled in the art as the "+3 binding pocket", which is the region of the SH2 domain that makes close contact with the +3 amino acid position of the signal transduction protein relative to the phosphotyrosine. The "+3 binding pocket" is also referred to herein as the "specificity-determining region" of the SH2 domain. As described above, this region preferably encompasses all or portions of the BG loop, the EF loop, strand βE, strand βD, and strand βD'.

Figure 4:
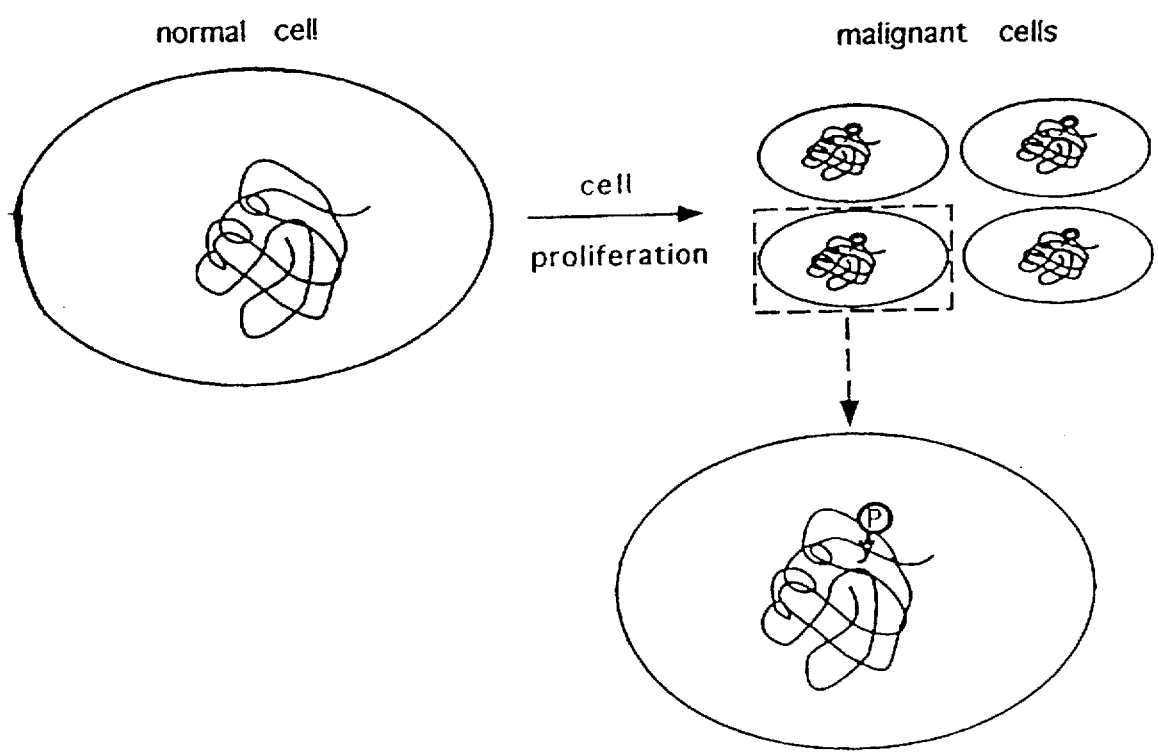
FIG. 4 is a schematic representation showing how tyrosine phosphorylation of a signal transduction protein can be responsible for malignant proliferation of a normal cell. The oval represents a cell membrane, the overlapping line represents a signal transduction protein, the encircled "P" represents phosphorylation, and the "y" represents a tyrosine residue. The dashed box and arrow indicate that an expanded view of the contents enclosed by the box is shown at the end of the arrow.
Figure 5A:
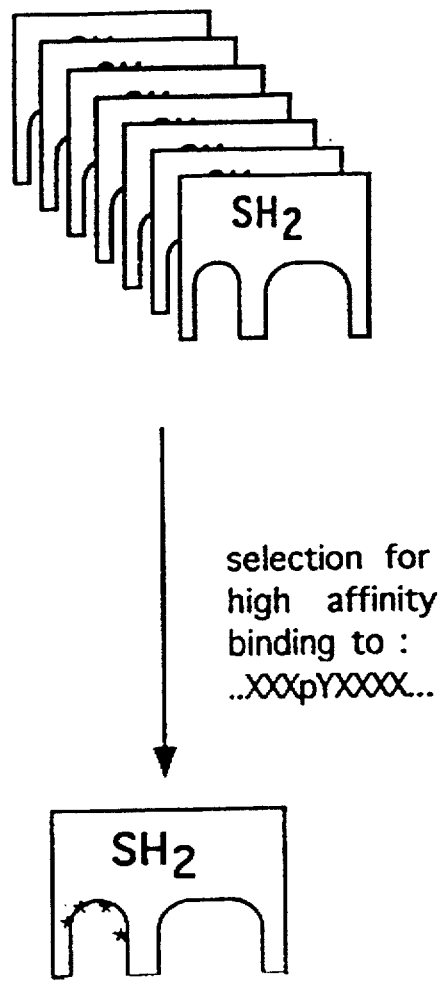
FIG. 5a and FIG. 5b are schematic representations showing two approaches for the design of modified SH2 domains. A new peptide binding specificity of an SH2 domain is engineered so that the peptide binding pocket binds to an aberrant tyrosine phosphorylated signal transduction protein.
Figure 5B:
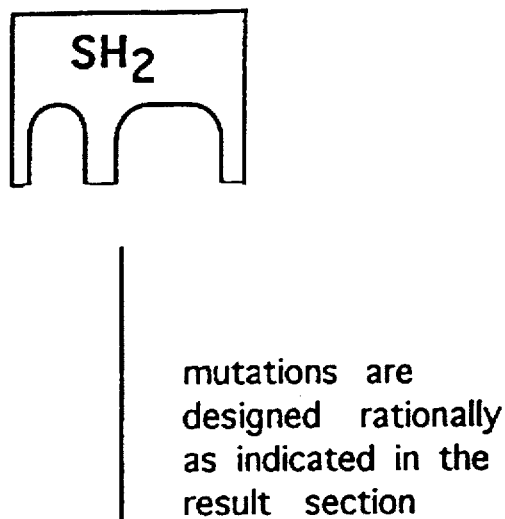
Figure 5B:
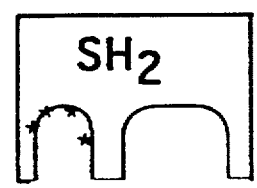

FIG. 4 shows schematically how tyrosine phosphorylation of a signal transduction protein is responsible for the malignant proliferation of cells. The engineering of SH2 domains to confer binding specificity for an aberrant tyrosine phosphorylated signal transduction protein or a protein other than the natural ligand is shown in FIGS. 5a and 5b. In FIG. 5a, an SH2 domain library containing random mutations around the specificity pocket is screened for high affinity peptide binding using a tyrosine phosphorylated peptide having the amino acid sequence proximal to the aberrant phosphorylated tyrosine of the signal transduction protein. In FIG. 5b mutations are rationally designed to engineer the required binding specificity.

Any SH2 domain can be tailored to recognize and bind a defined phosphorylation site by changing the amino acid sequences in the positions that determine specificity. For example, the src SH2 domain may be modified to bind the SH2 binding site of the signal transduction proteins IRS-1, PDGF receptor, CD28, and CD19. In addition, the SH2 domain may be engineered to bind this site with an affinity greater than the wild-type ligand. The SH2 domain containing the altered binding site will bind to the signal transduction protein, preventing or interfering with binding by the natural ligand.

Modifications resulting in addition of reactive group

Modification of the SH2 domain to include a reactive group should also be directed to a region of the SH2 domain that recognizes, binds, or influences the binding of the SH2 domain to the signal transduction protein, such as either the phosphotyrosine binding pocket or the "+3" binding pocket, preferably the phosphotyrosine binding pocket. The interaction between the reactive group on the SH2 domain and the signal transduction protein allows for the covalent modification of the signalling protein, permanently inactivating it, and increases the avidity of binding of the modified SH2 domain. For example, when bound to its ligand, the Ser177 residue of the src SH2 domain is within 3 angstroms of the phosphodiester bond of the phosphotyrosine contained in the signal transduction protein. Substitution of the Ser177 residue with a reactive chemical group, such as the amino acid cysteine, confers to the SH2 domain reactivity towards the phosphotyrosine, resulting in removal of the phosphate group, termination of the signal response and inactivation of the modified SH2 domain. As the serine corresponding to src Ser177 is conserved in all SH2 domains, this modification can be applied to other SH2 domains. Other reactive chemical groups may be introduced into this position using established genetic techniques by introducing a specific amber termination codon at this site. For example, a photoactivatable modified amino acid may be substituted for Ser177, or a photoreactive lysine group could be added, which would allow the activity of the modified SH2 domain to be regulated by UV light.

Figure 6A:
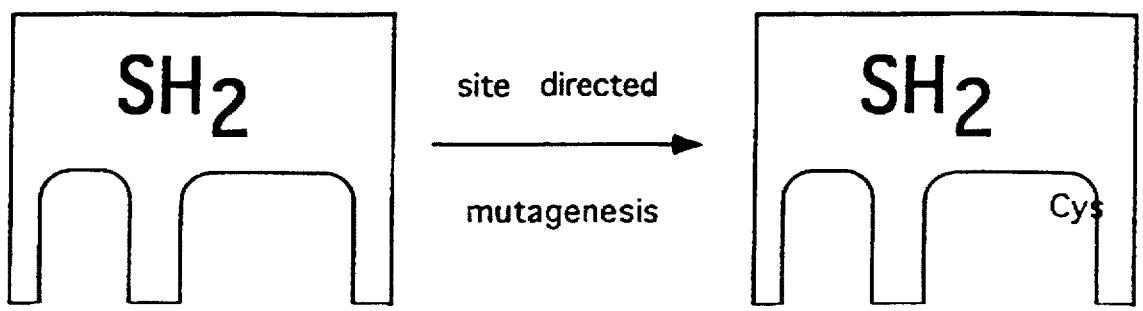
FIG. 6a is a schematic representation showing introduction of a cysteine residue in the phosphate binding pocket of an SH2 domain by site-directed mutagenesis.
Figure 6B:
FIG. 6b is a schematic representation showing that the side chain of the cysteine residue shown in FIG. 6a can be used to add a chemically reactive group, which is represented by an asterisk.

The introduction of a cysteine into the phosphate binding loop (or phosphotyrosine binding pocket) is shown schematically in FIG. 6a. The side chain of the cysteine or another residue side chain may be used to add a chemically reactive group as shown schematically in FIG. 6b.

Methods of Use

The modified SH2 domains are useful as molecular biology laboratory tools. For example, the modified SH2 domains are useful as laboratory tools to study signal transduction in general, such as for the identification of components of signal transduction pathways, the interactions and specificities of signal transduction proteins with SH2 domains, factors affecting signal transduction, and for determining whether a tyrosine residue on a signal transduction protein is phosphorylated or not in a particular cell or cell line.

Therapeutics

The modified SH2 domains are useful in methods for inactivating or inhibiting signal transduction proteins that contribute to diseases or disorders such as malignancies. The modified SH2 domains act by interfering with the signal generated by the signal transduction protein so that the signal is not transmitted to other components of the cell.

The modified SH2 domains may be administered by a delivery system such as liposome delivery systems or by gene therapy. For example, engineered SH2 domains, produced in vitro, may be administered in vehicles such as liposomes to deliver the modified proteins directly to the targeted cells, such as tumor cells. Alternatively, target cells may be infected with a recombinant virus containing the SH2 domain gene, or by inserting the SH2 domain gene sequence directly into target cells, to create recombinant cells expressing the modified SH2 domain. Site-specific gene transfer may be achieved by transfecting target cells in vivo, such as with the use of liposomes containing a modified SH2 domain expression vector plasmid.

In addition, nucleic acid sequences encoding the modified SH2 domains may be inserted into appropriate vectors used in gene therapy and delivered to the target cells as described in more detail below. Most preferably, the sequence encoding all or a portion of a modified SH2 domain is transferred into the target cells, such as cancer cells having an aberrant signal transduction protein by gene replacement, gene correction and gene augmentation.

Basically, the modified SH2 domain gene is inserted into cancer cells by first inserting the gene sequence into a retrovirus vector, such as a murine amphotropic retroviral vector. Preferably, the retrovirus vector is one that infects mammalian cells. Alternatively, the sequence may be inserted into an adenovirus-based viral vector system, preferably one that infects mammalian cells. Most preferably, the modified SH2 gene sequence is inserted into the vector pLNXSN, described by Miller, A. D., et al., (*Methods in Enzymology* 217:581(1993)), or is inserted into vectors having characteristics similar to the vector pLNXSN or derivatives thereof.

Engineered SH2 domain DNA may be transfected into cells by one of several standard published procedures to form stable transformants, including, for example, calcium phosphate precipitation, DEAE-Dextran, electroporation, and protoplast fusion. These methods are described in detail as follows:

Calcium phosphate precipitation: DNAs are co-precipitated with calcium phosphate, according to the method of Graham and VanDer in *Virology* 52, 456 (1973), before transfer into cells. 40–50 μg of DNA with salmon sperm or calf thymus DNA as carrier is used for $0.5 \times 10^6$ cells plated on a 100 mm dish. DNA is mixed with 0.5 ml of 2×Hepes solution (280 mM NaCl, 50 mM Hepes and 1.5 mM $Na_2HPO_4$, pH 7.0) to which an equal volume of 2×$CaCl_2$ (250 mM $CaCl_2$ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol in PBS for three minutes. After removing the glycerol, the cells are fed with Dulbecco's Minimal Essential Medium (DMEM) containing 10% fetal bovine serum and left in the incubator.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.* 1, 743 (1981).

Protein samples are prepared for Western blot analysis by lysing cells and separating the proteins by SDS-PAGE. The proteins are transferred to nitrocellulose by electroblotting as described by Ausubek, et al., *Current Protocols in Molecular Biology* (John Wiley and Sons, 1987). After blocking the filter with instant nonfat dry milk (1 g in 100 ml PBS), primary antibody is added to the filter and incubated for one hour at room temperature. The filter is washed thoroughly with phosphate buffered saline (PBS) and incubated with horseradish peroxidase (HRPO)-antibody conjugate for one hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

Target cells are then infected with the recombinant virus containing the gene, or by inserting the gene sequence directly into cells, to create recombinant cells expressing the modified SH2 domain. Alternatively, site-specific gene transfer is achieved by transfecting cells in vivo, such as with the use of liposomes containing a modified SH2 domain expression vector plasmid. The modified SH2 domain gene can be coupled to a gene for a enzyme such as beta-galactoside so that successful gene transfer can be observed by analysis by X-gal staining which reveals a blue coloration in the cells that have incorporated the genes. Alternatively, modified SH2 domain production, indicating successful transfer of the gene, can be detected with the aid of a monoclonal antibody, or modified SH2 domain mRNA can be detected using an oligonucleotide probe.

Administration of SH2 domains having alterations in binding specificity enable the targeting of a preselected signal transduction protein, such as an aberrant or a constitutively activated receptor. The binding of the natural SH2 domain ligand for the signal transduction protein is thereby impeded or blocked and the cascade of signalling events is inhibited or terminated.

Administration of SH2 domains having alterations in the SH2 domain resulting in the introduction of a reactive group provides an SH2 domain having the ability to react with the signal transduction protein, such as to dephosphorylate a phosphorylated signal transduction protein. Dephosphorylation also results in the inhibition or termination of the signal transduction cascade.

Drug Development

Engineered or modified SH2 domains may be used for drug development or drug screening. The modified SH2 domains may be used as suitable alternatives to natural SH2 domains when it is known that cell proliferation is caused by a phosphorylation event on a tyrosine residue but it is unclear which SH2 -containing protein is responsible for binding to the tyrosine residue and propagating the signal. For example, it is known that phosphorylation of a well-defined tyrosine proximal to the membrane on the interferon gamma receptor is responsible for interferon signalling. However, no SH2 -containing protein has yet been identified to associate with this particular phosphorylation site. SH2 domains with engineered specificity for this site could be used therapeutically as described above to block possible constitutive interferon signalling.

In addition, modified SH2 domains could be used to screen compounds such as the compounds contained in a library of compounds maintained by a major pharmaceutical company. Compound capable of blocking the phosphorylation site for signalling, such as interferon signalling, would be capable of blocking the responses of the ligand, such as interferon, and would therefore be useful as therapeutic agents. It will be understood by those skilled in the art that this rationale could be applied to any similar situation where constitutive phosphorylation of the tyrosine residue is the cause of the pathology.

Figure 7A:
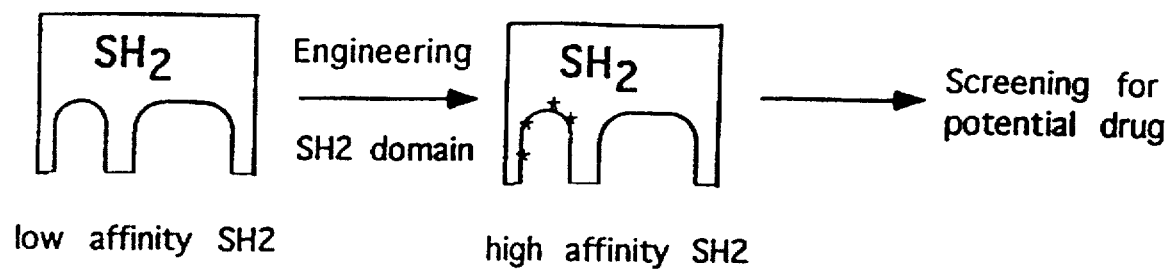
FIGS. 7a and 7b are schematic representations showing use of modified SH2 domains for drug screening. The asterisks represent mutations that have been engineered in the peptide binding specificity pocket of the SH2 domain to create high affinity binding for an aberrant phosphorylation site of a signal transduction protein to be inhibited. The binding of drug to the modified SH2 domain competes with the binding of the aberrant signal transduction protein to the non-modified SH2 domain, thereby preventing or retarding cell proliferation.
Figure 7B:
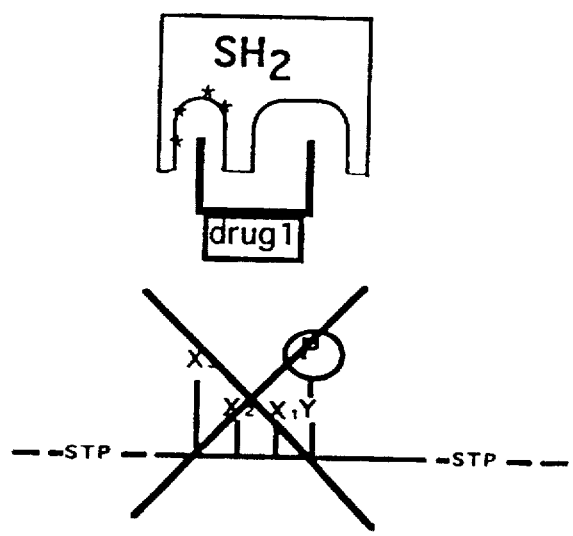

FIG. 7a shows schematically how an SH2 domain can be engineered so that it will bind to small organic or inorganic molecules with high affinity and can be used to screen for a potential therapeutic drug. When the molecule (or drug) binds to the high affinity SH2 domain, interactions between the SH2 domain and the signal transduction protein are blocked, as shown in FIG. 7b. A molecule capable of interfering with the communication of the aberrant phosphorylation state from the signal transduction protein to the engineered high affinity SH2 domain will be capable of competing with the natural target (containing the non-modified SH2 domain), thereby inhibiting or preventing cell proliferation.

Diagnostics

Figure 8:
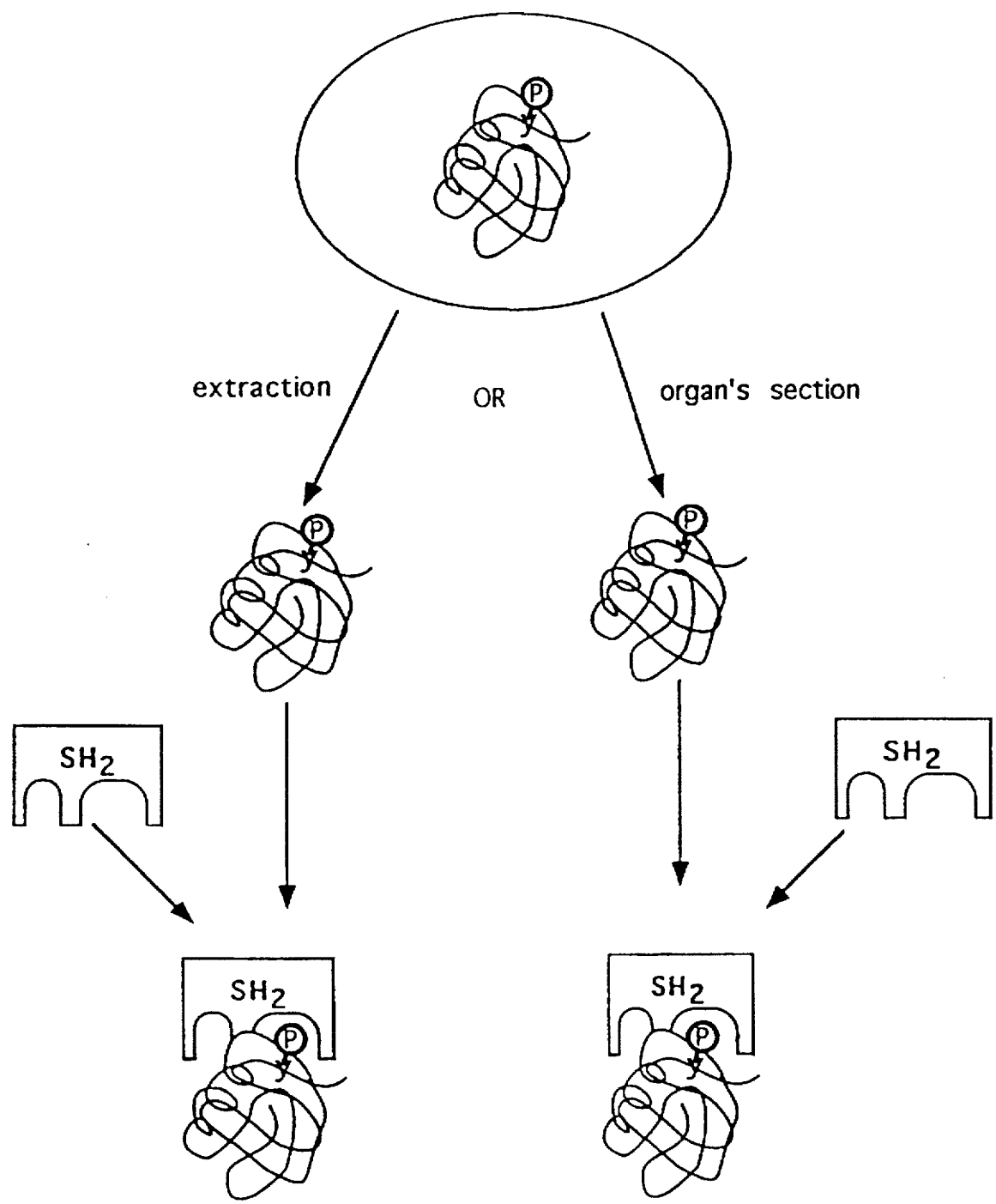
FIG. 8 is a schematic flow chart showing use of modified SH2 domains for cancer diagnosis. Cells containing the tyrosine phosphorylated signal transduction protein to be detected by the modified SH2 domain are obtained by extraction or organ sectioning. The oval represents a cell membrane, the overlapping line represents a signal transduction protein, the encircled "P" represents phosphorylation, and the "y" represents a tyrosine residue.

The modified SH2 domains having altered binding specificities are useful for in vitro diagnostics. The modified SH2 domain is labelled with a detectable label in accordance with methods well known to those skilled in the art, such as chemical conjugation, and reacted with cells taken from a cancer patient. The cells may be obtained by extraction from a biological fluid, biopsy, or organ section. Detection of the phosphorylated tyrosine of a cancer cell is shown schematically in FIG. 8.

Detection of the label indicates the presence of a particular signal transduction protein. The presence or absence of this protein may be used to diagnose the particular type of cancer or may be used to monitor the progress of therapy, regression or metastasis.

Suitable labels include biotin, which binds to streptavidin; digoxigenin, which binds to anti-digoxigenin; or 2,4-dinitrophenol (DNP), which binds to anti-DNP. The streptavidin or antibody molecule is conjugated to a detectable molecule, such as an enzyme that is then reacted with its substrate to produce a detectable reaction, such as a color change. Radioactivity or fluorogens can also be used to label the modified SH2 domains. Examples of fluorogens include fluorescein and derivatives, phycoerythrin, allophycocyanin, phycocyanin, rhodamine, Texas Red or other proprietary fluorogens. The fluorogens are generally attached by chemical modification and bind to a fluorogen-specific antibody, such as anti-fluorescein. It will be understood by those skilled in the art that the modified SH2 domains can also be labelled by incorporation of a modified amino acid containing any chemical group recognizable by specific antibodies. Other labels and methods of labelling proteins are well known to those skilled in the art.

The modified SH2 domains and methods of use will be further understood with reference to the following non-limiting examples.

EXAMPLE 1

Replacement of the Ser177 Residue of an SH2 Domain with Cysteine

The Ser177 residue of the src SH2 domain was modified by replacement with a cysteine residue, and the phosphatase activity of the modified SH2 domain was determined.

Materials and Methods

Oligonucleotide directed mutagenesis was used to modify the coding sequence of the src cDNA to substitute cysteine for the serine residue at position 177. The mutated cDNA was fused to sequences encoding glutathione S transferase, expressed in bacteria and the expressed protein was purified and tested for phosphatase activity in vitro. Phosphatase activity was assessed by measuring the ability of the purified protein to hydrolyze the substrate, p-nitrophenylphosphate (pNP) in accordance with the method of Pan, M. G., et al., *Science* 256:1215-1217 (1992). A glutathione S transferase fusion protein containing the wild-type src SH2 domain was used as a control.

Results

Addition of pNP-phosphate to the modified SH2 domain resulted in a dramatic increase in the release of pNP when compared with the unmodified control, namely a 330% to a 800% increase in pNP-ase activity was observed. These results indicate that the cysteine residue is reactive and is useful for the removal of phosphate groups from phosphorylated signal transduction proteins.

EXAMPLE 2

Engineering of SH2 Domains Having Different Binding Specificities

This experiment was designed to test whether the following secondary structures: the BG loop, the EF loop, or the βD strand, of the src SH2 domain are capable of conferring specificity for a particular signal transduction protein. The sequences of the src SH2 and the N-terminal SH2 domain of the P85 subunit of the PI-3 kinase were compared. Each has a distinct binding specificity. The src SH2 domain binds to the sequence pYEEI (Nucleotides 1 to 4 of SEQ ID NO:1). The p85 SH2 domain binds the sequence pYMDM (Nucleotides 1 to 4 of SEQ ID NO:2). Residues in the specificity-determining regions of the src SH2 domain were substituted for their corresponding residues from p85. The affinity of each mutated src protein was tested for the ability to bind to pYEEI (Nucleotides 1 to 4 of SEQ ID NO:1) and pYMDM (Nucleotides 1 to 4 of SEQ ID NO:2).

Materials and Methods

Oligonucleotide directed mutagenesis was used to substitute residues of src with corresponding residues from p85. The src mutant designated "M1" substituted isoleucine and phenylalanine for the tyrosine at position 202 (βD5) and arginine at position 205 (βD'1). The src mutant designated "M2" substituted leucine and alanine for glycine at position 237 (BG3) and leucine at position 238 (BG4). The src mutant "M3" substituted phenylalanine and serine for the isoleucine at position 214 (βE4) and threonine at position 215 (EF1) of src. In addition, all of the two by two combinations of these mutants were generated. Each was expressed in bacteria as glutathione S transferase fusion proteins, purified and tested for binding to pYEEI (Nucleotides 1 to 4 of SEQ ID NO:1) and pYMDM (Nucleotides 1 to 4 of SEQ ID NO:2) using surface plasmon resonance as described by Panayotou, G., *Mol. Cell. Biol.* 13:3567-3576 (1993).

Binding of mutated and wild-type SH2 domains from src and the p85 subunit of PI3-kinase to the phosphorylated YEEI peptide was determined as follows. The peptide pYEEISPK (SEQ ID NO:1) biotinylated on the C-terminal lysine residue was coupled onto a streptavidin coated sensor chip at a concentration of 20 pg/ml. Glutathione S transferase (GST) fusions of mutated and wild-type SH2 domains were injected at a flow rate of 5 µl/min. Protein concentrations for mutated src SH2 domains designated M1M3 (abbreviated as "13"), M1M2 (abbreviated as "12"), M2M3 (abbreviated as "23"), as well as the p85 SH2 domain were adjusted to obtain equivalent binding signals.

Binding of mutated and wild-type SH2 domains from src and the p85 subunit of PI3-kinase to phosphorylated YMDM peptide was measured as follows. The peptide pYMDMSPK (SEQ ID NO:2) biotinylated on the C-terminal lysine residue was coupled onto a streptavidin coated sensor chip at a concentration of 20 pg/ml. GST fusions of mutated and wild-type SH2 domains were injected at a flow rate of 5 µl/min. Protein concentrations used were as determined above for binding to the phosphorylated YEEI protein.

Binding of mutated and wild-type SH2 domains from src and the p85 subunit of PI3-kinase to phosphorylated YMDM peptide at equal protein concentration was measured as described above.

Results

Figure 9A:
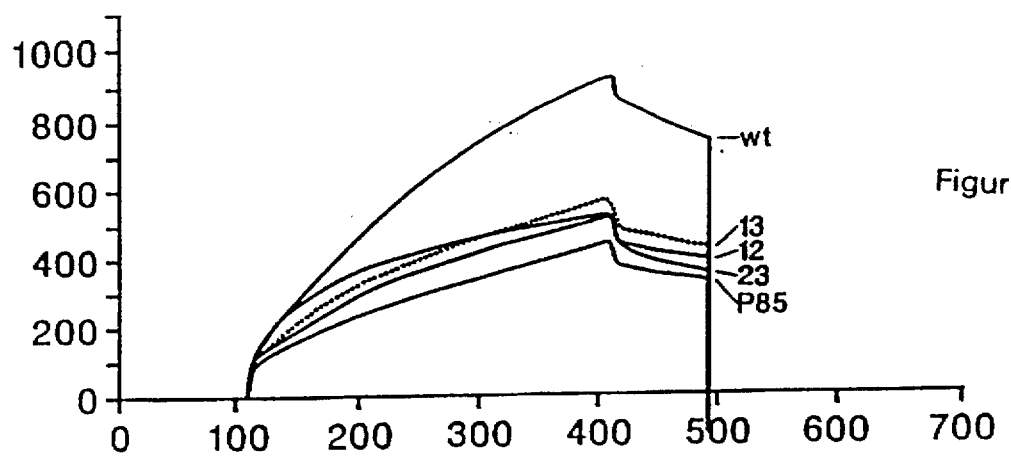
FIGS. 9a, 9b and 9c are graphs showing the specific binding of modified src SH2 domains to phosphorylated peptides.
Figure 9B:
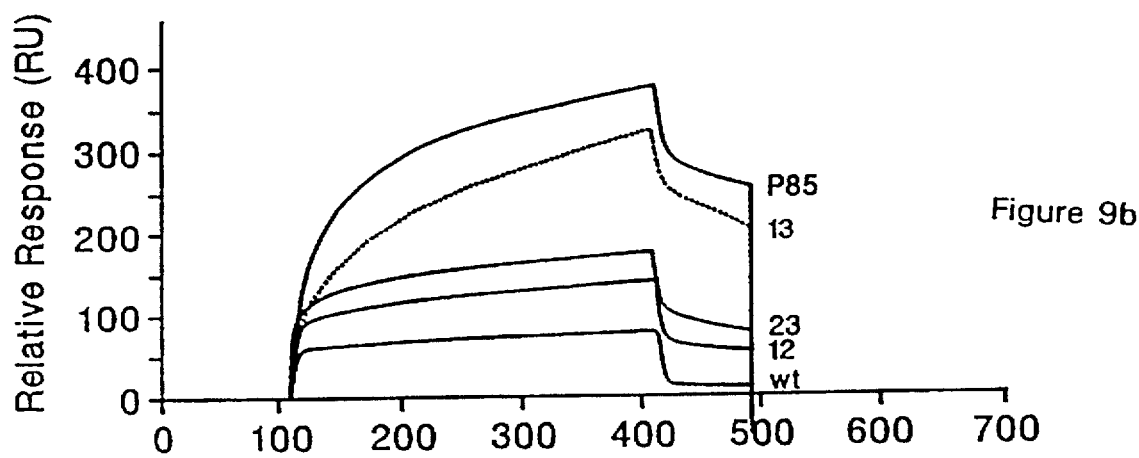
Figure 9C:
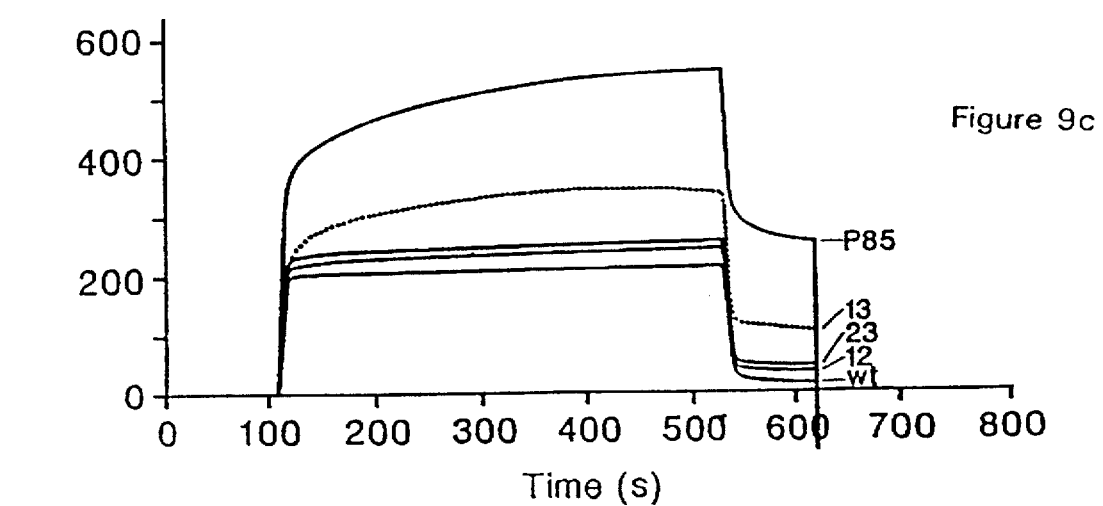

The src SH2 domains that contained the single sets of mutations (M1, M2, and M3) did not demonstrate a detectable increase in affinity for pYMDM. However, as shown in FIGS. 9a–c, all of the double mutants, M1M2, M1M3 and M2M3 showed reproducible and detectable increases in affinity towards the pYMDM peptide. The M1M3 had a significantly enhanced affinity towards the pYMDM peptide that compares with the level of affinity measured with the wild-type p85 SH2 domain.

These results demonstrate that a limited number of residues determine the specificity of SH2 domains and that modification of the EF1 loop, βE strand, and βD strand of the src SH2 domain can confer novel peptide binding specificity.

Modifications and variations of the modified SH2 domains and methods of use will be obvious to those skilled in the art from the foregoing detailed description. Such modifications and variations are intended to come within the scope of the appended claims.

We claim:

1. A modified SH2 domain comprising a binding site for a signal transduction protein wherein the amino acid corresponding to Ser177 in the src SH2 domain is replaced or modified such that the binding site reacts with a phosphorylated amino acid of the signal transduction protein and the modified SH2 domain is not an abl SH2 domain.

2. The modified SH2 domain of claim 1 having specificity to bind to a signal transduction protein that is not the natural ligand.

3. The modified SH2 domain of claim 1 wherein a cysteine replaces the amino acid corresponding to Ser177 in the src SH2 domain.

4. The modified SH2 domain of claim 1 wherein the phosphorylated amino acid is a phosphorylated tyrosine.

5. The modified SH2 domain of claim 3 wherein the SH2 domain is a src SH2 domain.

6. The modified SH2 domain of claim 1 labelled with a detectable label.

7. The modified SH2 domain of claim 1 wherein the binding site inactivates the signal transduction protein by removing a phosphate from the phosphorylated amino acid of the signal transduction protein.

8. A modified SH2 domain of claim 1 selected from the group consisting of src and other src family kinases, phospholipase C-γ1, the p85 subunit of phosphatidylinositol-3-OH kinase (PIK), ras guanine triphosphatase-activating protein (GAP), insulin receptor substrate-1 (IRS-1), protein-tyrosine phosphatases, grb-2, shc, ZAP-70, syk, and transcription factors of the Stat family.

9. The modified SH2 domain of claim 8 having specificity to bind to a signal transduction protein that is not the natural ligand.

10. The modified SH2 domain of claim 8 wherein a cysteine replaces the amino acid corresponding to Ser177 in the src SH2 domain.

11. The modified SH2 domain of claim 8 wherein the phosphorylated amino acid is a phosphorylated tyrosine.

12. The modified SH2 domain of claim 10 wherein the SH2 domain is a src SH2 domain.

13. The modified SH2 domain of claim 8 labelled with a detectable label.

14. The modified SH2 domain of claim 8 wherein the binding site inactivates the signal transduction protein by removing a phosphate from the phosphorylated amino acid of the signal transduction protein.

15. A modified SH2 domain of claim 1 wherein the amino acid corresponding to Ser177 in the src SH2 domain is replaced with an amino acid residue other than a cysteine residue.

16. The modified SH2 domain of claim 15 having specificity to bind to a signal transduction protein that is not the natural ligand.

17. The modified SH2 domain of claim 15 wherein the phosphorylated amino acid is a phosphorylated tyrosine.

18. The modified SH2 domain of claim 15 wherein the SH2 domain is a src SH2 domain.

19. The modified SH2 domain of claim 15 labelled with a detectable label.

* * * * *